United States Patent
Kataoka et al.

(10) Patent No.: US 10,067,127 B2
(45) Date of Patent: Sep. 4, 2018

(54) IMMUNOLOGICAL DETECTION METHOD AND IMMUNOLOGICAL DETECTION REAGENT

(71) Applicant: SEKISUI MEDICAL CO., LTD., Tokyo (JP)

(72) Inventors: Chie Kataoka, Tokyo (JP); Hiroshi Takahashi, Tokyo (JP); Tadaaki Yoshida, Tokyo (JP); Yoshimasa Banba, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 330 days.

(21) Appl. No.: 14/431,888

(22) PCT Filed: Sep. 30, 2013

(86) PCT No.: PCT/JP2013/076585
§ 371 (c)(1),
(2) Date: Mar. 27, 2015

(87) PCT Pub. No.: WO2014/051144
PCT Pub. Date: Apr. 3, 2014

(65) Prior Publication Data
US 2015/0253322 A1 Sep. 10, 2015

(30) Foreign Application Priority Data
Sep. 28, 2012 (JP) .................................. 2012-218089

(51) Int. Cl.
*G01N 33/543* (2006.01)

(52) U.S. Cl.
CPC .............................. *G01N 33/54393* (2013.01)

(58) Field of Classification Search
CPC ............................................... G01N 33/54393
See application file for complete search history.

(56) References Cited

U.S. PATENT DOCUMENTS

| 2011/0165701 A1 | 7/2011 | Takahashi et al. |
| 2011/0212462 A1 | 9/2011 | Duffy et al. |
| 2016/0011181 A1* | 1/2016 | Takahashi ........ G01N 33/57434 435/7.92 |

FOREIGN PATENT DOCUMENTS

| EP | 0 566 205 A1 | 10/1993 |
| EP | 1 767 942 A1 | 3/2007 |
| JP | 2-152999 A | 6/1990 |
| JP | 7-12818 A | 1/1995 |
| JP | 9-288108 A | 11/1997 |
| JP | 11-287801 A | 10/1999 |
| JP | 11-337551 A | 12/1999 |
| JP | 2007-127438 A | 5/2007 |
| JP | 2007-163319 * | 6/2007 |
| JP | 2010-254663 A | 11/2010 |
| WO | WO 2010/026758 A1 | 3/2010 |

OTHER PUBLICATIONS

Ferenčík, "Antigen-antibody reactions in vitro," in Handbook of Immunochemistry, 1993, pp. 292-308, retrieved from https://link.springer.com/content/pdf/10.1007/978-94-011-1552-0_11.pdf on Aug. 10, 2017.*
Macoto, JP 2007-163319, published Jun. 28, 2007; English translation.*
Dolk et al., "Induced refolding of a temperature denatured llama heavy-chain antibody fragment by its antigen," 2005, vol. 59, issue 3, pp. 555-564.*
International Search Report, issued in PCT/JP2013/076585, dated Dec. 24, 2013.
English translation of International Preliminary Report on Patentability and Written Opinion dated Apr. 9, 2015, in PCT International Application No. PCT/JP2013/076585.
Machine English translation of JP 7-12818 A, Jan. 17, 1995.
Machine English translation of JP 11-287801 A, Oct. 19, 1999.
Machine English translation of JP 11-337551 A, Dec. 10, 1999.
Machine English translation of JP 2007-127438 A, May 24, 2007.
Machine English translation of JP 2010-254663 A, Nov. 11, 2010.
Machine English translation of JP 2-152999 A, Jun. 12, 1990.
Machine English translation of JP 9-288108 A, Nov. 4, 1997.
Extended European Search Report dated Apr. 4, 2016, in European Patent Application No. 13840321.7.

* cited by examiner

*Primary Examiner* — Galina Yakovleva
(74) *Attorney, Agent, or Firm* — Birch, Stewart, Kolasch & Birch, LLP

(57) ABSTRACT

An object of the present invention is to provide a method of detecting an analyte (antigen) in a sample by an antigen-antibody reaction with an antibody fragment including an antigen binding region for the analyte antigen (hereinafter "an antibody fragment comprising an antigen binding region for an analyte antigen" will simply be referred to as "an antibody fragment against antigen"), the method suppressing nonspecific reaction that is caused by antibody fragments. More specifically, provided is a method of detecting an analyte antigen in a sample by an antigen-antibody reaction with an antibody fragment against antigen, the method comprising the steps of: a) bringing a sample into contact with a denatured antibody fragment; and b) bringing the sample into contact with the antibody fragment immobilized on an insoluble carrier after the step of a), the method suppressing nonspecific reaction.

13 Claims, 1 Drawing Sheet

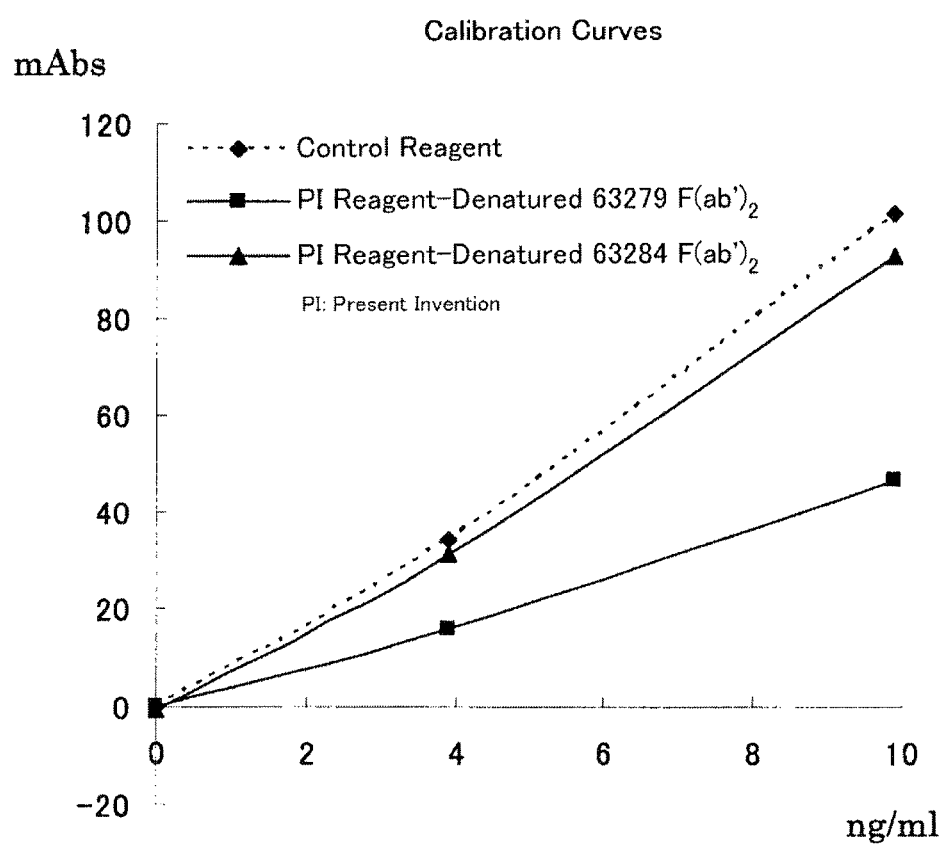

IMMUNOLOGICAL DETECTION METHOD AND IMMUNOLOGICAL DETECTION REAGENT

TECHNICAL FIELD

The present invention relates to a suppressing method and an agent for suppressing nonspecific reaction (a nonspecific-reaction suppressant) and an immunoassay using the same, and more specifically to a suppressing method and an agent for suppressing nonspecific reaction characteristic of an immunoassay using antibody fragment immobilized on the insoluble carriers.

BACKGROUND ART

One of the general methods for measuring an analyte in a specimen is immunoassay using antibodies for analyte (antigen) in the field of clinical chemistry. Particularly, immunoagglutination methods and immunochromatographic methods using antibodies immobilized on the insoluble carriers have the advantage in sensitivity and usability, so they are universal measurement methods applied to various clinical examination items.

Due to the recent improvements in measurement accuracy, to avoid nonspecific reactions in immunoassays is a problem in the development of in vitro diagnostic reagents. Nonspecific reaction is a phenomenon in which some kind of factor in a specimen reacts with an antibody that is used as a constituent component of the reagent employing as a principle an immunoassay and generates a false signal, which results in interference with correct measurement. The heterophile antibody and rheumatoid factor (RF) were found to be a causal factor of nonspecific reaction.

Heterophile antibody is a collective term for human antibodies exhibiting reactivity to an animal-derived antibody that is a main component for making up an immunoassay, and HAMA (human anti-mouse antibody) is known as a representative antibody. Since it is suggested that heterophile antibody may be produced by antigen sensitization under unconscious situations such as diet, contact with an animal, and administration of a biological drug and that an antibody in a sample from a human unexposed to an antigen can exhibits heterophilicity, the cause thereof is currently not clarified in detail or in a unified way. On the other hand, since rheumatoid factor appears in rheumatoid arthritis patients and is known as recognizing the Fc region of immunoglobulins (antibodies), the concept of rheumatoid factor is considered to be different from that of heterophile antibody; however, both have a common characteristic in terms of reactivity to animal-derived antibodies and it is known that both are actually human IgG or IgM (so-called autoantibody) as described in Non-Patent Document 1.

In a conventional method, antibody fragments (defined later), Fab or F(ab')$_2$, acquired by removing Fc region, are used as antibodies used for in vitro diagnostic reagent to reduce nonspecific reaction, and such method is particularly effective in the suppression of the effects of rheumatoid factor. Additionally, a heterophilic blocking reagent HBR, which contains as a component anti-human IgM monoclonal antibodies described in Non-Patent Documents 2 and 3, is commercialized by SCANTIBODIES as an additive agent suppressing nonspecific reaction due to heterophile antibody binding to Fab. Other methods have also been devised, including a method described in Patent Document 1 comprising adding a polyclonal antibody to IgM class natural antibody prepared from an animal of the same species as that of the antibody used for measurement, a method described in Patent Document 2 comprising adding various animal antibodies to recognition regions of rheumatoid factor, and a method of suppressing nonspecific reaction described in Patent Document 3 comprising using a single kind of anti-human IgM monoclonal antibody capable of agglutinating human IgM.

However, nonspecific reaction cannot sufficiently be suppressed only by the conventional countermeasures and it has been found out that the countermeasures themselves cause nonspecific reaction in some specimens.

CITATION LIST

Patent Literature

Patent Document 1: JP H11-287801 A
Patent Document 2: JP H07-012818 A
Patent Document 3: WO2010/026758

Non Patent Literature

Non-Patent Document 1: Clinical Chemistry; Vol. 23 Supplement 175a-1 to 175a-10 (1994)
Non-Patent Document 2: Advertising Material for Heterophilic Blocking Reagent HBR (NAGASE & CO., LTD., 1993)
Non-Patent Document 3: CLIN. CHEM. 45/7,942-956 (1999)

SUMMARY OF INVENTION

Technical Problem

The present invention relates to a suppressing method and a nonspecific-reaction suppressant and an immunoassay using the same and, more specifically, the problem to be solved by the present invention is to provide a method and an agent for suppressing nonspecific reaction characteristic of an immunoassay using an antibody fragment immobilized on an insoluble carrier.

Solution to Problem

As a result of intensive studies for solving the problem, the present inventors have found that, in a measurement method using an insoluble carrier on which an antibody fragment is immobilized, nonspecific reaction can be suppressed by bringing a sample exhibiting nonspecific reaction that cannot be suppressed by conventional countermeasures using a full-length, non-fragmented, antibody (hereinafter also referred to as an intact antibody) into contact with a denatured antibody fragment before or at the same time with bringing the sample into contact with insoluble carriers on which an antibody fragment is immobilized, thereby completing the present invention. An object of the present invention therefore relates to a method of suppressing nonspecific reaction using a denatured antibody fragment.

The present inventors have surprisingly found that, even if the denatured antibody fragment and the antibody fragment immobilized on the insoluble carriers are not derived from the same full-length antibody, the nonspecific-reaction suppressing effect of the object of the present invention is exerted as long as the antibody fragments are antibodies to an analyte antigen. Another object of the present invention therefore relates to a nonspecific-reaction suppressant containing a denatured antibody fragment and a further object relates to an immunoassay and an immunoassay reagent using the suppressant.

Specifically, the present invention has the following configuration.

[1] A method of detecting an analyte antigen in a sample by an antigen-antibody reaction with an antibody fragment comprising an antigen binding regions for the analyte antigen (hereinafter "an antibody fragment(s) comprising an antigen binding region(s) for an/the analyte antigen" will simply be referred to as "an antibody fragment(s)"), the method comprising the steps of:

a) bringing a sample into contact with denatured antibody fragment;

b) bringing the sample into contact with the antibody fragment immobilized on an insoluble carrier at the same time with the step of a) or after the step of a).

[2] The detection method of [1], wherein the denatured antibody fragment recognizes an epitope same as or different from that of the antibody fragment immobilized on an insoluble carrier.

[3] The detection method of [1] or [2], wherein the antibody fragment immobilized on an insoluble carrier of b) comprises at least two kinds of antibody fragments having antigen-binding regions different to each other and independently immobilized on insoluble carriers.

[4] A method of suppressing nonspecific reaction in a method of detecting an analyte antigen in a sample by an antigen-antibody reaction with an antibody fragment, the method comprising the steps of:

a) bringing a sample into contact with a denatured antibody fragment;

b) bringing the sample into contact with the antibody fragment immobilized on an insoluble carrier at the same time with the step of a) or after the step of a).

[5] The method of suppressing nonspecific reaction of [4], wherein the denatured antibody fragment recognizes an epitope same as or different from that of the antibody fragment immobilized on an insoluble carrier.

[6] The method of suppressing nonspecific reaction of [4] or [5], wherein the antibody fragment immobilized on an insoluble carrier of b) comprises at least two kinds of antibody fragments having antigen-binding regions different to each other and independently immobilized on insoluble carriers.

[7] The method of suppressing nonspecific reaction of any one of [4] to [6], wherein nonspecific reaction is caused by the antibody fragment used for the measurement.

[8] The method of suppressing nonspecific reaction of any one of [4] to [7], wherein nonspecific reaction is a reaction that cannot be suppressed by an agent for suppressing nonspecific-reaction containing a full-length antibody.

[9] The method of suppressing nonspecific reaction of [8], wherein the full-length antibody is a full-length anti-human IgG antibody or an anti-human IgM antibody or an anti-human IgA antibody.

[10] The method of suppressing nonspecific reaction of [9], wherein the full-length antibody is a monoclonal antibody produced by hybridoma FERM BP-11134.

[11] The method of suppressing nonspecific reaction of [9], wherein the agent for suppressing nonspecific-reaction containing a full-length antibody is HBR (SCANTIBODIES).

[12] A reagent for detecting an analyte antigen in a sample by an antigen-antibody reaction, the reagent comprising:

1) an insoluble carrier on which an antibody fragment to the analyte antigen is immobilized; and 2) a denatured antibody fragment to the analyte antigen.

[13] The reagent of [12], wherein the denatured antibody fragment recognizes an epitope same as or different from that of the antibody fragment immobilized on an insoluble carrier.

[14] The reagent of [12] or [13], wherein the antibody fragment immobilized on an insoluble carrier of 1) comprises at least two kinds of antibody fragments having antigen-binding regions different to each other and independently immobilized on insoluble carriers.

[15] The reagent of [12] or [13], further comprising 3) an agent for suppressing nonspecific-reaction containing a full-length antibody.

[16] An agent for suppressing nonspecific reaction in a method of detecting an analyte antigen in a sample by an antigen-antibody reaction with an antibody fragment, the agent for suppressing nonspecific reaction containing a denatured antibody fragment as an active ingredient.

Advantageous Effects of Invention

A method of avoiding nonspecific reaction of the present invention enables suppression of nonspecific reaction that cannot be suppressed by conventional methods using intact antibodies.

An immunoassay method and an immunoassay reagent containing the nonspecific-reaction suppressant of the present invention can give more accurate measurement values because of the suppression of nonspecific reaction that cannot be avoided by known suppressants.

BRIEF DESCRIPTION OF DRAWINGS

FIG. 1 is a diagram of calibration curves of reagents (Example 2).

DESCRIPTION OF EMBODIMENTS (Antibody Fragments)

Antibody fragments are fragments derived from antibodies and including a Fab structure that is an antigen binding region, and Fab and F(ab')$_2$ are frequently used. The antibody fragments are typically created by removing Fc region through enzymatic treatment of intact antibodies (non-fragmented full-length antibodies) with pepsin or papain in the usual manner, or may be synthesized or altered by gene recombination without particular limitation.

(Insoluble Carriers)

Insoluble carriers are not particularly limited and are preferably selected from insoluble carrier particles made of materials including latex made of synthetic polymer, metal colloid, silica, alumina, carbon black, ceramic, or magnetic material. The synthetic polymer is preferably one or more polymers selected from polystyrene, styrene-sulfonic acid copolymer, styrene-methacrylic acid copolymer, acrylonitrile-butadiene-styrene copolymer, vinyl chloride-acrylic ester copolymer, and vinyl acetate-acrylic ester copolymer. In immunochromatographic methods such as those using a membrane to detect a ternary complex of a labelled antibody, an antigen and a detection antibody with a detection line on the membrane, a labeled portion of the labeled antibody and the membrane of a detection line portion is considered to be comprised in the insoluble carriers with the immobilized antibody fragment of the present invention.

(Immobilization of Antibody Fragments on Carriers)

A method of immobilization of an antibody fragment on insoluble carriers is not particularly limited and can be implemented by both physical and chemical frequently used binding methods.

In the case of detection using an immunoagglutination method, the antibodies which are immobilized on the insoluble carriers must include at least two kinds of antibodies for recognizing different epitopes on an antigen if the antigen is not a polyvalent antigen; in the present invention, one or more kinds of the antibody fragments may be used; all the antibodies may be antibody fragments; and Examples described later exemplify the case that two kinds of antibody fragments are independently immobilized on the insoluble carriers.

(Nonspecific Reaction)

A method of suppressing nonspecific reaction of the present invention can effectively suppress nonspecific reaction that does not occur in an immunoassay using intact antibodies immobilized on insoluble carriers but is expressed in the method using antibody fragments immobilized on insoluble carriers yielded from the intact antibodies, and that cannot be suppressed by conventional methods using the intact antibodies. Examples of conventional nonspecific-reaction suppressants using intact antibodies include agents suppressing nonspecific reactions due to HAMA, heterophile antibody, and rheumatoid factor (RF) and include, for example, a suppressant containing a full-length anti-human IgG antibody or anti-human IgM antibody, and more specifically, a suppressant containing as an active ingredient a heterophilic blocking reagent HBR (SCANTIBODIES) or a monoclonal antibody produced by the hybridoma FERM BP-11134.

(Denatured Antibody Fragment)

A method for denaturing antibody fragments is not particularly limited and can be implemented by applying heating, acid, alkali, a reducing agent, chaotropic salts, etc., which are typically used for usual denaturation of proteins, and a treatment method resulting in irreversible denaturation effects is particularly preferable. With regard to the order of fragmentation and denaturation, the full-length antibodies may be denatured after fragmentation or the full-length antibodies may be fragmented after denaturation. In this description, "a/the denatured antibody fragment(s)" may also be referred to as "denatured antibody fragment" or "denaturation antibody fragment" and these terms are used as synonyms unless otherwise stated.

The degree of denaturation of antibody fragments may be at any level as long as the reactivity to the antigen is lost or the reactivity is reduced as compared to the antibody fragments on the insoluble carriers without suppressing the main reaction for antigen measurement to a practical level or less. At the time of denaturation operation, a protein component, such as BSA, sericin, and blocking peptide fragments (TOYOBO CO., LTD), and glycerol can be allowed to coexist for adjusting the level of denaturation.

(Use)

The nonspecific-reaction suppressant of the present invention is applicable to any immunoassays using antibody fragments immobilized on insoluble carriers and may preferably be used as an agent for pretreatment of a specimen or as a portion of constituent components of immunoassays/reagents. The immunoassays specifically include a generally-used particle enhanced immunoagglutination method, an immunochromatographic method that is a simple examination method, and chemiluminescent- and fluorescent-enzyme methods using dedicated equipment.

(Additives)

The nonspecific-reaction suppressant and an immunoassay reagent containing the suppressant of the present invention may contain buffers, proteins, peptides, amino acids, nucleic acids, lipids, phospholipids, sugars, inorganic salts, surfactants, preservatives, etc as long as the nonspecific-reaction suppressing effect thereof is not inhibited.

(Measurement Object Substance or Analyte Antigen)

The method of suppressing nonspecific reaction of the present invention is applicable to any substance as long as antibody fragments can be created the antigen of which is a measurement object substance. The measurement object substance may be proteins, peptides, amino acids, nucleic acids, lipids, sugars, nucleic acids, and hapten and is not particularly limited as long as the molecules are theoretically measurable. Examples include CRP (C-reactive protein), Lp(a), MMP-3 (matrix metalloproteinase-3), anti-CCP (cyclic citrullinated peptide), antibodies, anti-phospholipid antibodies, RPR, type IV collagen, PSA, BNP (brain natriuretic peptide), NT-proBNP, insulin, microalbumin, cystatin C, RF (rheumatoid factor), CA-RF, KL-6, PIVKA-II, FDP, D-dimer, SF (soluble fibrin), TAT (thrombin-antithrombin III complex), PIC, PAI, a factor XIII, pepsinogen I/II, phenytoin, phenobarbital, carbamazepine, valproic acid, and theophylline.

Although the concentration of analyte antigen for which suppression of nonspecific reaction can be achieved varies depending on the kind of antigens, the kind of antibodies, and other conditions, it is particularly desirable that the effect is produced within a range including a normal concentration of the analyte antigen in serum, for example, and if the object of measurement is PSA, it is desirable that the suppressing effect is exerted at a concentration level near 4 ng/mL, which is defined as a clinical cutoff value, such as 2 to 5 ng/mL as in Examples described later.

The detection of the present invention includes qualitative detection for examining the presence/absence of an analyte antigen in a sample and also means quantitative detection (i.e., measurement) such as quantitatively examining the abundance of an analyte antigen in a sample. Therefore, in this description, terms "detection", "quantitation", and "measurement" are intended to be broadly construed as including the proof of the presence and/or the quantification of an antigen that is an analyte unless otherwise stated.

EXAMPLES

Although a part of the present invention will be described in detail by using examples of an immunoassay and an immunoassay reagent utilizing a method of suppressing nonspecific reaction using denatured antibody fragments and a nonspecific-reaction suppressant containing denatured antibody fragments, the present invention is not limited thereto.

Example 1: Analysis of Specimen Exhibiting Nonspecific Reaction and Suppression of Nonspecific Reaction by the Present Invention (1) Preparation of Antibody Fragments Antibody fragments were produced and purified in a usual manner from anti-PSA (prostate specific antigen) monoclonal antibody 63279 IgG (monoclonal antibody produced by a hybridoma Accession No. FERM BP-11454).

In particular, after a 63279 IgG solution and a 0.2 M citric acid solution (pH 3.5) were mixed in equal amount and pepsin was added in a one one-hundred-thirtieth (1/130)

amount (w/w) of IgG, the solution was incubated for 4 hours at 37° C. and a 2 M Tris solution was then added in a one tenth (1/10) volume for neutralization. The final solution was subjected to a gel filtration method to acquire purified 63279 F(ab')$_2$.

(2) Preparation of Antibody-Bound Latex Solution

A 0.4% latex solution (with an average particle diameter of 300 nm) diluted to respective concentrations by using a 20 mM glycine buffer solution (pH 9.0) and a 63279 F(ab')$_2$ solution prepared to an absorbance of 0.4 Abs/mL at a wavelength of 280 nm were mixed in equal amounts (1 part by volume+1 part by volume) and stirred for about one hour, and then, 0.1 part by volume of 10% BSA was added and the solution was stirred for about one hour. After supernatant was removed by centrifugation, the precipitate was resuspended in a 5 mM MOPS buffer solution (pH 7.0) and adjusted to an absorbance of 1.5 Abs/mL at a wavelength of 600 nm to acquire a 63279 F(ab')$_2$-bound latex solution. A 63279 IgG-bound latex solution was prepared as a control by using 63279 IgG (full-length antibody without fragmentation) instead of 63279 F(ab')$_2$.

(3) Preparation of Treatment Solution Containing Nonspecific-Reaction Suppressing Substance Made of Intact Antibodies A treatment solution was prepared by adding nonspecific-reaction suppressing substances, i.e., HBR (SCANTIBODIES) and an anti-IgM monoclonal antibody 73224 (monoclonal antibody produced by a hybridoma Accession No. FERM BP-11134), to a HEPES buffer solution containing potassium chloride, BSA, and PVP-K90, to final concentrations of 100 μg/mL. Both of these nonspecific-reaction suppressing substances are full-length IgG, i.e., intact antibodies.

(4) Preparation of Denatured Antibody Fragment

A PBS solution containing 63279 F(ab')$_2$ at an absorbance of 4.0 Abs/mL at a wavelength of 280 nm was heated at 65° C. for 30 minutes to acquire a denatured 63279 F(ab')$_2$ solution.

(5) Method of Analysis

A serum exhibiting PSA-positive reaction (SLR Research, Lot. 101409 with a indicated PSA concentration of 2.36 ng/mL; hereinafter referred to as an indicated value) was used as a sample, and the treatment solution adjusted in (3) described above and the antibody-bound latex solution adjusted in (2) described above were added to the sample to confirm occurrence of nonspecific reaction from the changes in absorbance. Since PSA is not a polyvalent antigen having a plurality of the same epitopes in the molecule, a single kind of antibody-bound latex alone cannot form agglutination even when PSA in the sample reacts with the antibody-bound latex and, therefore, absorbance normally does not change. Thus, it is considered that the changes in absorbance generated in this method of analysis are attributable to a nonspecific agglutination. Analysis conditions were as follows.

(Analysis Conditions)

Analysis Apparatus: Hitachi 7180 Automatic Analyzer

S/R ratio: sample-treatment solution-antibody-bound latex solution=9.6-60-60 (in μL)

Measurement wavelength: 800/570 nm (sub wavelength/main wavelength)

Analysis Method: two-point end method (Photometric Point 19-34)

(6) Confirmation of Effect of Denatured Antibody Fragments of the Present Invention The serum specimen Lot. 101409 which exhibited an increase in absorbance in the analysis of (5) described above and in which nonspecific reaction was recognized was appropriately diluted with a PBS solution containing the denatured 63279 F(ab')$_2$ or a PBS solution without the denatured 63279 F(ab')$_2$ to acquire a specimen or a control sample subjected to measurement, respectively.

The measurement result is shown in Table 1.

From this result, the occurrence of nonspecific reaction with the 63279 F(ab')$_2$-bound latex was confirmed in the specimen Lot. 101409 exhibiting an increase in absorbance. The occurrence of nonspecific reaction was not recognized with 63279 IgG-immobilized latex used as a control and the occurrence of nonspecific reaction with the 63279 F(ab')$_2$-immobilized latex was not able to be suppressed by a nonspecific-reaction suppressing substance (HBR or anti-IgM monoclonal antibody) made of intact antibodies (data not shown), and therefore, it was inferred that the reaction was nonspecific reaction caused by antibody fragments.

When the specimen Lot. 101409 was analyzed after being diluted twice with a PBS solution containing the denatured 63279 F(ab')$_2$ at an absorbance of 0.4 Abs/mL at a wavelength of 280 nm, the change in absorbance was substantially zero and it was confirmed that nonspecific reaction was suppressed. When the specimen was diluted twice by a PBS solution without the denatured 63279 F(ab')$_2$, nonspecific reaction was not suppressed although a reduction in absorbance itself due to dilution was recognized.

TABLE 1

|  | 63279F(ab')$_2$-binding latex | 63279 IgG-binding latex |
|---|---|---|
| Original serum | 32.0 | −1.1 |
| PI (trmt. w. denatured 63279 F(ab')$_2$) | −1.4 |  |
| Control (two-fold dilution with PBS) | 8.5 |  |
|  |  | Unit (mAbs) |

PI: Present invention,
trmt.: treatment,
w.: with

Example 2: Immunoassay Reagent Containing Agent for Suppressing Nonspecific-Reaction of the Present Invention (1) Searching for Denatured Antibody Fragments Exhibiting Nonspecific-Reaction Suppressing Effect Denatured F(ab')$_2$ of various anti-PSA monoclonal antibodies was prepared in accordance with Example 1 in search of antibody fragments exhibiting the nonspecific-reaction suppressing effect, and denatured 63284 F(ab')$_2$ was acquired. The 63284-antibody can be combined with the 63279-antibody used in Example 1 to perform sandwich ELISA measurement and therefore recognizes an epitope different from that of the 63279-antibody.

(2) Preparation of First Reagent Solution

A first reagent solution was acquired by adding denatured 63279 F(ab')$_2$ or denatured 63284 F(ab')$_2$ at an absorbance of 0.0003 Abs/mL at a wavelength of 280 nm to the treatment solution described in Example 1. The treatment solution without denatured antibody fragments was used as a first reagent solution of a control.

(3) Preparation of Second Reagent Solution

The 63279 F(ab')$_2$-immobilized latex solution prepared in Example 1 and a 63291 (monoclonal antibody produced by a hybridoma Accession No. FERM BP-11455) F(ab')$_2$-immobilized latex solution prepared in the same way were each adjusted with a 5 mM MOPS buffer solution (pH 7.0) to an absorbance of 1.5 Abs/mL at a wavelength of 600 nm and were mixed in equal amount to acquire a second reagent solution. By combining two kinds of latex each binding an antibody fragment recognizing different epitopes, agglutination with PSA in a sample can be formed, which enables calculation of a PSA concentration.

(4) Measurement Method

The two kinds of the first reagent solutions (containing denatured 63279 F(ab')$_2$ or denatured 63284 F(ab')$_2$) and the second reagent solution were combined as measurement reagents and calibration curves were constructed in advance by using a PSA calibrator (SEKISUI MEDICAL Co., Ltd.) under the following conditions to measure the PSA concentration of the specimen Lot. 101409. The analysis conditions were as follows.

(Analysis Conditions)

Analysis Apparatus: Hitachi 7180 Automatic Analyzer

S/R ratio: sample-first reagent solution-second reagent solution=8-76-76 (in μL)

Measurement wavelength: 800/570 nm (sub-wavelength/main wavelength)

Method of Analysis: two-point end method (Photometric Point 19-34)

Calibrator concentration: 0, 3.9, 9.9 (ng/mL)

Arithmetic expression: spline

The PSA concentration of the specimen Lot. 101409 was acquired by reference to an indicated value.

(5) Result

FIG. 1 shows the calibration curves of the reagents.

The reagent containing the denatured 63279 F(ab')$_2$ have an absorbance reduced by about half as compared to the control reagent without the denatured antibody fragments. It was assumed that this occurred because the denatured 63279 F(ab')$_2$ competed with the 63279 F(ab')$_2$-immobilized latex and inhibited agglutination because of a residual reactivity to PSA. On the other hand, in the case of using the first reagent solution containing the denatured 63284 F(ab')$_2$ which recognizes an epitope different from those recognized by the antibody fragments (63279 F(ab')$_2$ and 63291 F(ab')$_2$) making up the measurement system, the sensitivity was reduced by about 10%.

The measurement values of the specimen Lot. 101409 with the reagents are shown in Table 2.

While the control reagent resulted in a measurement value higher than the indicated value by 30% or more, it was confirmed that the both reagents of the present invention containing the denatured antibody fragments suppress the effect of nonspecific reaction. A normal concentration of PSA is 4 ng/mL or less and it is important from a clinical viewpoint to secure the accuracy of measurement values near this concentration.

Particularly, it is preferable that antibody fragments, such as the denatured 63284 F(ab')$_2$, which recognizes epitope different from that recognized by antibody fragments used as the main component of an immunoassay reagent, are used as the agent for suppressing nonspecific-reaction of the present invention because the effect on reagent sensitivity is small.

TABLE 2

| Indicated PSA conc. | Control reagent measurement value | Measurement value of reagent of the PI | |
|---|---|---|---|
| | | Dn. 63279F(ab')$_2$ | Dn. 63284 F(ab')$_2$ |
| 2.36 | 3.2 | 2.5 | 2.7 |
| | | | Unit (ng/mL) | conc.: concentration,
PI: present invention,
Dn.: Denatured

Example 3: Analysis of Specimen with Nonspecific Reaction and Suppression of Nonspecific Reaction by the Present Invention 2

(1) Preparation of Solution of Antibody Fragment-Immobilized Latex

Antibody fragments were produced and purified from anti-MMP-3 monoclonal antibody 82208 IgG (monoclonal antibody produced by a hybridoma Accession No. FERM BP-11517) in accordance with the method of Example 1 and were adjusted with a 5 mM MOPS buffer solution (pH 7.0) to an absorbance of 3.0 Abs/mL at a wavelength of 600 nm to acquire a solution of 82208 F(ab')$_2$-immobilized latex.

(2) Preparation of Treatment Solution Containing Nonspecific-Reaction Suppressing Substance Made of Intact Antibodies A treatment solution was prepared by adding HBR (SCANTIBODIES) and the anti-IgM monoclonal antibody 73224, which are nonspecific-reaction suppression substances, to a Tris buffer solution containing sodium chloride and BSA to final concentrations of 100 μg/mL.

(3) Preparation of Denatured Antibody Fragments

A denatured 82208 F(ab')$_2$ solution was acquired in accordance with the method described in Example 1.

(4) Sample and Denatured Antibody Fragment Treatment

A serum which causes nonspecific reaction with the 82208 F(ab')$_2$-immobilized latex was selected from RF positive serums (TRINA) and was diluted ten times with a PBS solution containing denatured 82208 F(ab')$_2$ at an absorbance of 6.0 Abs/mL at a wavelength of 280 nm or a PBS solution to acquire a specimen or a control sample subjected to measurement.

(5) Method of Analysis

The treatment solution adjusted in (2) and a solution of the antibody fragment-immobilized latex adjusted in (1) were added to the specimen or the control sample adjusted in (4) to confirm occurrence of nonspecific reaction and the suppressing effect of the present invention from the changes in absorbance. It is considered that the changes in absorbance occurring in this analysis are attributable to nonspecific agglutination as were the case with Example 1. Analysis conditions were as follows.

(Analysis Conditions)

Analysis Apparatus: Hitachi 7180 Automatic Analyzer

S/R ratio: sample-treatment solution-solution of antibody-immobilized latex=2.0-100-33 (in μL)

Measurement wavelength: 800/570 nm (sub-wavelength/main wavelength)

Analysis Method: two-point end method (Photometric Point 19-34)

(6) Result

The result is shown in Table 3.

While an increase in sensitivity due to nonspecific reaction was recognized in the control sample, the change in absorbance was substantially zero in the specimen and the suppression of nonspecific reaction was confirmed.

TABLE 3

| | 82208F(ab')$_2$-binding latex |
|---|---|
| Original serum | 140.3 |
| PI (trmt, w. den. 82208 F(ab')2) | 0.3 |
| Ctrl. (ten-fold dilution with PBS) | 9.8 |
| | Unit (mAbs) |

PI: Present invention,
trmt.: treatment,
w.: with,
Ctrl.: Control,
den.: denatured From the results of Examples 1 to 3, it was confirmed that the method of suppressing nonspecific reaction of the present invention is widely applicable regardless of the types of the detection target antigen (analyte) and the types of antibody fragments.

INDUSTRIAL APPLICABILITY

The method of suppressing nonspecific reaction of the present invention enables suppression of nonspecific reaction that is caused by antibody fragments and that cannot be suppressed by conventional methods using intact antibodies.
Accession Number
[Reference to Deposited Biological Material]
(1) Hybridoma 63279 producing the 63279-antibody
i) Name and address of the depository institution where the biological material has been deposited
International Patent Organism Depositary, National Institute of Advanced Industrial Science and Technology
Central 6, 1-1-1 Higashi, Tsukuba, Ibaraki, Japan (postal code: 305-8566)
ii) Date of biological material deposit in the depository institution of i)
19 Feb. 2010 (original deposit date)
31 Jan. 2012 (date of transfer from the original deposit to the deposit under the Budapest Treaty)
iii) Accession number for the deposit assigned by the depository institution of i).
FERM BP-11454
(2) Hybridoma 63291 producing the 63291-antibody
i) Name and address of the depository institution where the biological material has been deposited
International Patent Organism Depositary, National Institute of Advanced Industrial Science and Technology
Central 6, 1-1-1 Higashi, Tsukuba, Ibaraki, Japan (postal code: 305-8566)
ii) Date of biological material deposit in the depository institution of i)
19 Feb. 2010 (original deposit date)
31 Jan. 2012 (date of transfer from the original deposit to the deposit under the Budapest Treaty)
iii) Accession number for the deposit assigned by the depository institution of i).
FERM BP-11455
(3) Hybridoma 82208 producing the 82208-antibody
i) Name and address of the depository institution where the biological material has been deposited
International Patent Organism Depositary, National Institute of Advanced Industrial Science and Technology
Central 6, 1-1-1 Higashi, Tsukuba, Ibaraki, Japan (postal code: 305-8566)
ii) Date of biological material deposit in the depository institution of i)
27 Jan. 2012 (original deposit date)
22 Nov. 2012 (date of transfer from the original deposit to the deposit under the Budapest Treaty)
iii) Accession number for the deposit assigned by the depository institution of i).
FERM BP-11517
(4) Hybridoma 73224 producing the anti-IgM antibody
i) Name and address of the depository institution where the biological material has been deposited
International Patent Organism Depositary, National Institute of Advanced Industrial Science and Technology
Central 6, 1-1-1 Higashi, Tsukuba, Ibaraki, Japan (postal code: 305-8566)
ii) Date of biological material deposit in the depository institution of i)
19 Sep. 2008 (original deposit date)
9 Jun. 2009 (date of transfer from the original deposit to the deposit under the Budapest Treaty)
iii) Accession number for the deposit assigned by the depository institution of i).
FERM BP-11134

The invention claimed is:
1. A method of detecting an analyte antigen in a sample by an antigen-antibody reaction with at least two kinds of monoclonal antibody fragments comprising antigen binding regions for the analyte antigen different to each other, the method comprising the steps of:
  a) bringing a sample into contact with a denatured monoclonal antibody fragment comprising an antigen binding region for the analyte antigen;
  b) bringing the sample into contact with the at least two kinds of monoclonal antibody fragments comprising antigen binding regions for the analyte antigen different to each other immobilized on respective insoluble carriers at the same time with the step of a) or after the step of a); and
  c) detecting the analyte antigen using an immunoagglutination method,
  wherein the denatured monoclonal antibody fragment recognizes an epitope different from epitopes recognized by the at least two kinds of monoclonal antibody fragments immobilized on the insoluble carriers.
2. The method of detecting an analyte antigen of claim 1, wherein said denatured monoclonal antibody fragment is a denatured Fab or F(ab')$_2$ fragment.
3. The method of detecting an analyte antigen of claim 1, wherein said denatured monoclonal antibody fragment is contained in a treatment solution and wherein said at least two kinds of monoclonal antibody fragments are contained in an antibody-bound latex solution.
4. The method of detecting an analyte antigen of claim 1, wherein said denatured monoclonal antibody fragment is a denatured Fab or F(ab')$_2$ fragment, wherein said denatured monoclonal antibody fragment is contained in a treatment solution, and wherein said at least two kinds of monoclonal antibody fragments are contained in an antibody-bound latex solution.
5. A method of suppressing a nonspecific reaction in a method of detecting an analyte antigen in a sample by an antigen-antibody reaction with at least two kinds of monoclonal antibody fragments comprising antigen binding regions for the analyte antigen different to each other, the method comprising the steps of:
  a) bringing a sample into contact with a denatured monoclonal antibody fragment comprising an antigen binding region for the analyte antigen;
  b) bringing the sample into contact with the at least two kinds of monoclonal antibody fragments comprising antigen binding regions for the analyte antigen different to each other immobilized on respective insoluble carriers at the same time with the step of a) or after the step of a),
  wherein the denatured monoclonal antibody fragment recognizes an epitope different from epitopes recognized by the at least two kinds of monoclonal antibody fragments immobilized on the insoluble carriers.
6. The method of suppressing a nonspecific reaction of claim 5, wherein said denatured monoclonal antibody fragment is a denatured Fab or F(ab')$_2$ fragment.

7. The method of suppressing a nonspecific reaction of claim 5, wherein said denatured monoclonal antibody fragment is contained in a treatment solution and wherein said at least two kinds of monoclonal antibody fragments are contained in an antibody-bound latex solution.

8. The method of suppressing a nonspecific reaction of claim 5, wherein said denatured monoclonal antibody fragment is a denatured Fab or F(ab')$_2$ fragment, wherein said denatured monoclonal antibody fragment is contained in a treatment solution, and wherein said at least two kinds of monoclonal antibody fragments are contained in an antibody-bound latex solution.

9. A reagent for detecting an analyte antigen in a sample by an antigen-antibody reaction with at least two kinds of monoclonal antibody fragments comprising antigen binding regions for the analyte antigen different to each other, the reagent comprising:
  1) the at least two kinds of monoclonal antibody fragments comprising antigen binding regions for the analyte antigen different to each other immobilized on respective insoluble carriers; and
  2) a denatured monoclonal antibody fragment comprising an antigen binding region for the analyte antigen, wherein the denatured monoclonal antibody fragment recognizes an epitope different from epitopes recognized by the at least two kinds of monoclonal antibody fragments immobilized on the insoluble carriers.

10. The reagent of claim 9, further comprising 3) a nonspecific-reaction suppressant containing a full-length antibody.

11. The reagent for detecting an analyte antigen of claim 9, wherein said denatured monoclonal antibody fragment is a denatured Fab or F(ab')$_2$ fragment.

12. The reagent for detecting an analyte antigen of claim 9, wherein said denatured monoclonal antibody fragment is contained in a treatment solution and wherein said at least two kinds of monoclonal antibody fragments are contained in an antibody-bound latex solution.

13. The reagent for detecting an analyte antigen of claim 9, wherein said denatured monoclonal antibody fragment is a denatured Fab or F(ab')$_2$ fragment, wherein said denatured monoclonal antibody fragment is contained in a treatment solution, and wherein said at least two kinds of monoclonal antibody fragments are contained in an antibody-bound latex solution.

\* \* \* \* \*